(12) United States Patent
Egnelöv et al.

(10) Patent No.: US 8,382,793 B2
(45) Date of Patent: Feb. 26, 2013

(54) INTRODUCER SHEATH

(75) Inventors: Per Egnelöv, Uppsala (SE); Fredrik Preinitz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 361 days.

(21) Appl. No.: 10/341,599

(22) Filed: Jan. 14, 2003

(65) Prior Publication Data
US 2004/0138674 A1    Jul. 15, 2004

(51) Int. Cl.
*A61B 17/08* (2006.01)
(52) U.S. Cl. .......................... 606/213; 606/108
(58) Field of Classification Search ............. 606/213, 606/142, 139, 108, 232; 604/264, 532
See application file for complete search history.

(56) References Cited

U.S. PATENT DOCUMENTS

| | | | | |
|---|---|---|---|---|
| 3,565,074 A * | 2/1971 | Foti | ........................... | 604/164.11 |
| 4,629,450 A | 12/1986 | Suzuki et al. | | |
| 4,744,364 A * | 5/1988 | Kensey | ........................ | 606/213 |
| 4,852,568 A * | 8/1989 | Kensey | ........................ | 606/213 |
| 4,890,612 A * | 1/1990 | Kensey | ........................ | 606/213 |
| 5,061,274 A | 10/1991 | Kensey | | |
| 5,282,827 A | 2/1994 | Kensey et al. | | |
| 5,290,310 A * | 3/1994 | Makower et al. | ........... | 606/213 |
| 5,292,309 A * | 3/1994 | Van Tassel et al. | .......... | 604/117 |
| 5,320,639 A * | 6/1994 | Rudnick | ...................... | 606/213 |
| 5,411,520 A * | 5/1995 | Nash et al. | .................... | 606/213 |
| 5,441,517 A | 8/1995 | Kensey et al. | | |
| 5,531,759 A * | 7/1996 | Kensey et al. | ................. | 606/213 |
| 5,618,272 A * | 4/1997 | Nomura | .................... | 604/166.01 |
| 5,645,566 A * | 7/1997 | Brenneman et al. | .......... | 606/213 |
| 5,649,959 A * | 7/1997 | Hannam et al. | ............... | 606/213 |
| 5,814,073 A * | 9/1998 | Bonutti | ........................ | 606/232 |
| 5,836,956 A | 11/1998 | Buelna et al. | | |
| 5,846,253 A * | 12/1998 | Buelna et al. | ................. | 606/148 |
| 5,871,474 A * | 2/1999 | Hermann et al. | ............. | 604/256 |
| 5,957,952 A * | 9/1999 | Gershony et al. | ............ | 606/213 |
| 6,004,547 A * | 12/1999 | Rowe et al. | ................. | 424/78.04 |
| 6,090,130 A | 7/2000 | Nash et al. | | |
| 6,162,192 A * | 12/2000 | Cragg et al. | .................... | 604/15 |
| 6,287,322 B1 | 9/2001 | Zhu et al. | | |
| 6,315,787 B1 * | 11/2001 | Tsugita et al. | ................ | 606/213 |
| 6,328,757 B1 * | 12/2001 | Matheny | ........................ | 606/213 |
| 6,383,208 B1 * | 5/2002 | Sancoff et al. | ................ | 606/213 |
| 6,468,292 B1 * | 10/2002 | Mollenauer et al. | .......... | 606/213 |
| 6,475,177 B1 * | 11/2002 | Suzuki | ........................... | 604/11 |
| 6,547,806 B1 * | 4/2003 | Ding | ............................. | 606/213 |
| 6,682,489 B2 | 1/2004 | Tenerz et al. | | |

(Continued)

FOREIGN PATENT DOCUMENTS

DE    44 29 647 A1    2/1996
EP    0 941 697 A1    9/1999

(Continued)

*Primary Examiner* — Darwin Erezo
(74) *Attorney, Agent, or Firm* — Foley & Lardner LLP

(57) ABSTRACT

The invention provides an introducer sheath (1, 21, 51), whose distal end is to be positioned inside a vessel (10, 32, 62), at a predetermined distance from the wall (9, 31, 61) of the vessel (10, 32, 62). The introducer sheath (1, 21, 51) comprises a distal portion (2, 22, 52) with a first diameter and a proximal portion (3, 23, 53) with a second diameter, the first diameter being smaller than the diameter of the puncture hole and the second diameter being larger than the diameter of the puncture hole.

20 Claims, 3 Drawing Sheets

U.S. PATENT DOCUMENTS 6,695,867 B2 * 2/2004 Ginn et al. .................. 606/213
6,790,220 B2 * 9/2004 Morris et al. ................ 606/213

FOREIGN PATENT DOCUMENTS

| | | |
|---|---|---|
| EP | 1 169 968 B1 | 1/2002 |
| EP | 1 254 634 B1 | 11/2002 |
| JP | 60-234671 A | 11/1985 |
| JP | 8-173438 A | 7/1996 |
| JP | 8-509392 A | 10/1996 |
| JP | 11-042233 A | 2/1999 |
| JP | 2002-253556 A | 9/2002 |
| WO | WO 94/17738 A | 8/1994 |
| WO | WO 95/13021 A1 | 5/1995 |
| WO | WO 00/78226 A1 | 12/2000 |

* cited by examiner

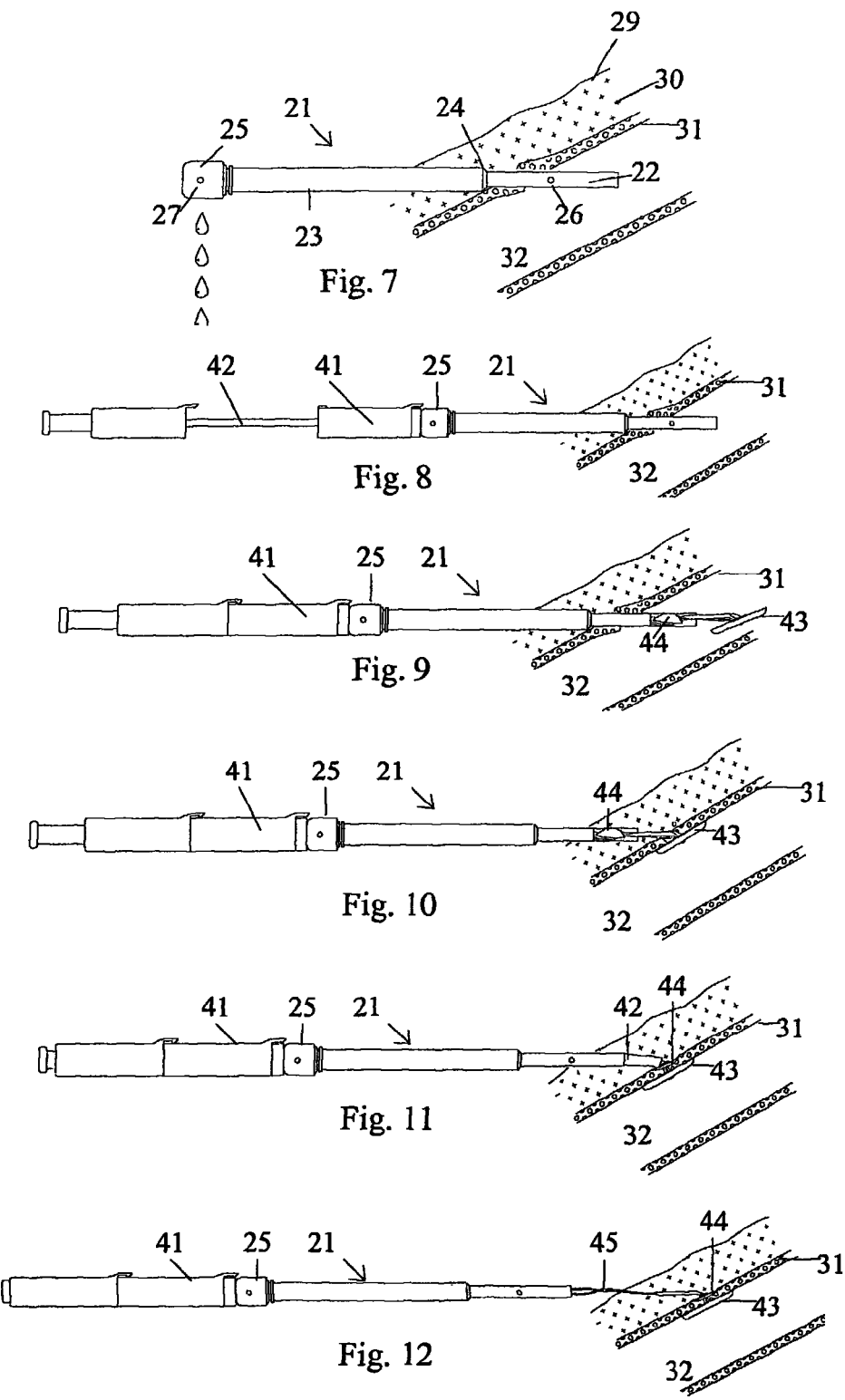

INTRODUCER SHEATH

FIELD OF THE INVENTION

The present invention relates generally to an introducer sheath to be used together with a sealing device in the sealing of a percutaneous puncture in a vessel, and more particularly to an introducer sheath being provided with an enlarged portion, which, during introduction into the puncture, stops against the vessel wall, so that the sealing device can be deployed at the desired location inside the vessel.

BACKGROUND OF THE INVENTION

A system for sealing a percutaneous puncture in a vessel may comprise an introducer sheath; and if the system belongs to the class of sealing devices wherein an inner seal is deployed inside the vessel, the distal portion of this introducer sheath extends through the vessel wall and into the vessel. During the introduction phase, the inner seal is folded inside the introducer, and to ensure proper unfolding of the inner seal, the inner seal has to be deployed some distance away from the vessel wall before the inner seal is retracted to be securely seated against the inner surface of the vessel wall. In other words, the distal end of the introducer sheath should be positioned at a desired location inside the vessel, with a known distance from the vessel wall, which, in turn, implies that the position of the vessel wall has to be determined.

An example of such a puncture closure system is disclosed in U.S. Pat. No. 6,090,130. This closure system comprises a vessel locator that includes means for enabling blood from an artery to flow therethrough, so that the position of the artery wall can be determined. Basically, the vessel locator comprises an introducer sheath and a dilator provided with a canal, through which blood can flow from a hole provided in the distal portion of the vessel locator to the proximal portion, where a user can observe a flow of blood out from a hole provided in the proximal portion. In order to correctly position the introducer sheath, the user has to perform several steps. First the introducer sheath is inserted into the artery such that blood can be observed at the proximal end of the introducer sheath. The introducer sheath is then retracted until the flow of blood out of the proximal end just stops, which indicates that the distal end of the introducer sheath has just left the arterial lumen. Thereafter, the introducer sheath is reinserted approximately 10 mm into the puncture to ensure that the distal end of the introducer sheath is at the desired location within the artery. Blood flow should be re-established from the proximal end at this time. From this point, the introducer sheath must be kept fixed.

This known vessel locator and the corresponding way of determining the position of the vessel wall have at least the following disadvantages. It is a messy procedure, with a rather large amount of blood flowing from the distal end of the introducer sheath. Secondly, and more importantly, it can, in praxis, be difficult to exactly determine the position at which the flow of blood just stops, i.e. for some patients the transition from a large flow of blood to essentially no flow of blood is not a readily observable discrete transition but a gradual transition, which makes it difficult to accurately determine the exact position of the vessel wall. Since the determination of the position of the vessel wall is the starting point for the reinsertion of the introducer sheath, the position of the distal end of the introducer sheath suffers from the same uncertainty. Furthermore, the somewhat arbitrary 10 mm reinsertion of the introducer sheath enhances this uncertainty. Finally, it should be noted that a user has to hold the introducer sheath fixedly without any assistance from a natural stop, i.e. the introducer sheath is free to move in the distal direction as well as in the proximal direction.

SUMMARY OF THE INVENTION

An object of the present invention is therefore to provide an improved introducer sheath, the distal end of which is to be positioned at a predetermined location in relation to a vessel wall and with which it is possible to overcome or reduce the disadvantages of the known device and method described above.

The present introducer sheath can, but is not limited to, be used together with the sealing and wound closure device shown in WO 0078226 A1, and the reader is referred to this reference for additional information about the closure system as a whole.

In a first embodiment, the introducer sheath according to the present invention has a distal portion with a first diameter and a proximal portion with a second diameter, the second diameter being larger than the first diameter. The diameter of the distal portion is smaller than the diameter of a puncture hole in the wall of a vessel, thereby allowing the distal portion to be inserted through the puncture hole and into the vessel. The diameter of the enlarged proximal portion, on the other hand, is larger than the diameter of the puncture hole, so that, during introduction of the introducer, the enlarged portion stops against the vessel wall. By choosing a suitable length for the distal portion, an inner seal introduced in the introducer can be deployed at the desired location inside the vessel.

In another embodiment, the introducer sheath is further provided with a canal that connects a first hole in the distal portion of the introducer sheath with a second hole in the proximal portion of the introducer sheath. Preferably, the distance from the first, distal hole to the edge of the enlarged proximal portion corresponds to the thickness of the wall of a blood vessel. With such an arrangement, the correct positioning of the introducer sheath can be verified by observing a flow of blood out from the second hole in the proximal portion of the introducer sheath.

BRIEF DESCRIPTION OF THE DRAWINGS

FIG. 7 shows the introducer sheath of FIG. 6 inserted into a blood vessel.

FIGS. 8-12 illustrate schematically the steps in a sealing operation that follows upon the positioning operation.

DETAILED DESCRIPTION OF THE PREFERRED EMBODIMENTS

Figure 1:
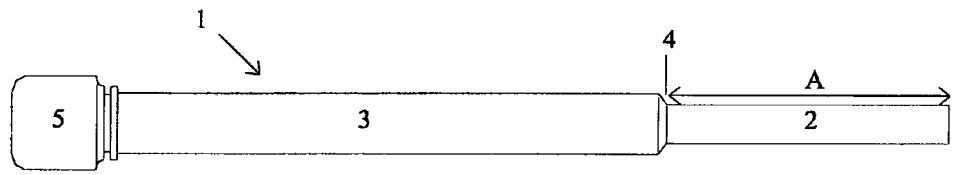
FIG. 1 shows a first embodiment of an introducer sheath according to the present invention.

A first embodiment of an introducer sheath 1 is shown in FIG. 1. The introducer sheath 1 has a distal portion 2 with a first diameter and a proximal portion 3 with a second diameter, the second diameter being larger than the first diameter. The distal edge of the proximal portion 3 has been marked with 4, and the distance from the distal end of the introducer sheath 1 to the edge 4 of the proximal portion 3 is denoted with the letter A. This distal edge 4, which also may be referred to as a transition portion, of the introducer sheath 1 can be a step or other type of sudden increase (e.g. a steep ramp) in diameter and is designed such that at least a portion of the step or sudden increase abuts a vessel wall and prevents the proximal portion 3 from entering the vessel. The purposes of these distal and proximal portions 2, 3 as well as the proper choice of the length A will be described below. The proximal end of the introducer sheath 1 is provided with a hub 5 for connection to some kind of closure and sealing system, such as the closure and sealing system disclosed in EP 1169968 B1. The introducer sheath 1 can be made from plastic, metal, or any other suitable material.

The special features and advantages of the introducer sheath according to the present invention will now be described with reference to the steps in a specific method for positioning the distal end of the introducer sheath at a desired location inside a blood vessel. It should, however, be understood that other positioning methods, which involve other steps, could be used, and that the introducer sheath according to the present invention is not limited to be used in blood vessels.

Figure 2:
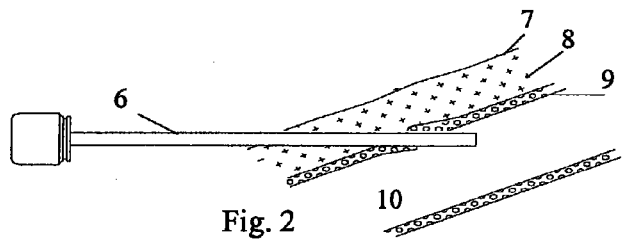
FIG. 2 illustrates schematically a blood vessel in which an introducer has been inserted.

FIG. 2 illustrates a situation in which a medical intravascular operation has been completed and only an introducer 6 is left in place. The introducer 6, which is not a part of the present invention, is inserted in a puncture hole that extends from the skin 7 of a patient, through tissue 8 and through the wall 9 of a blood vessel 10. After the completion of the medical operation, the puncture hole has to be closed, and FIG. 3 to FIG. 5 illustrate the steps in a positioning operation that precedes the actual sealing operation, which for the sake of clarity is illustrated in FIG. 8 to FIG. 12.

Figure 3:
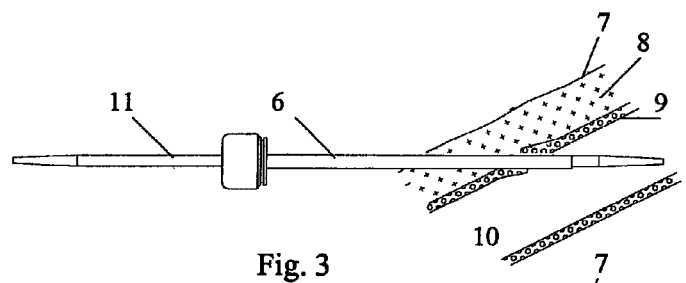
FIG. 3 illustrates the first step in a positioning operation where the distal end of an introducer sheath according to the present invention is going to be placed at a desired location inside the blood vessel.

The first step in the positioning of an introducer sheath according to the present invention is illustrated in FIG. 3. In the first step, a dilator 11 is inserted into the existing introducer 6.

Figure 4:
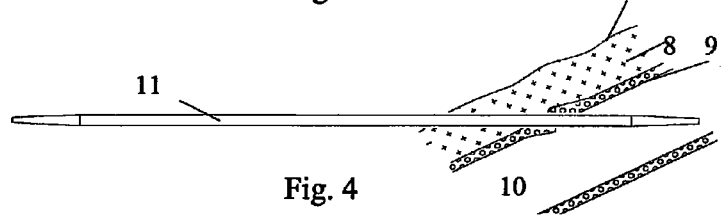
FIG. 4 illustrates the second step in the positioning operation.

In the second step of the positioning operation, the introducer 6 is retracted over the dilator 11 and can then be disposed, so that only the dilator 11 is left in place in the puncture hole, as is illustrated in FIG. 4.

Figure 5:
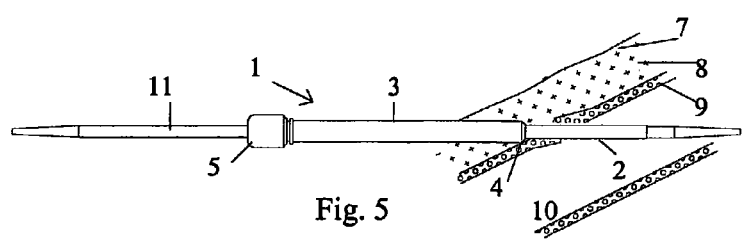
FIG. 5 illustrates the third step in the positioning operation.

In FIG. 5, the third step of the positioning operation is illustrated. In this step, in which the advantages of the present invention are exploited, the introducer sheath 1 of FIG. 1 is passed over the dilator 11. As can be seen from FIG. 5, the diameter of the distal portion 2 is smaller than the diameter of the puncture hole in the wall 9 of the blood vessel 10, whereas the diameter of the proximal portion 3 is larger than the diameter of the puncture hole in the wall 9 of the blood vessel 10. During the introduction of the introducer sheath 1, the introducer sheath 1 is advanced over the dilator 11 until the edge 4 of the enlarged proximal portion 3 stops against the vessel wall 9, with the distal portion 2 being inserted into the vessel 10. In a subsequent step (not shown), the dilator 11 is then retracted inside the introducer sheath 1 and can be disposed, thereby leaving only the introducer sheath 1 inserted in the puncture hole. Preferably, the length A of the distal portion 2, i.e. the distance from the distal end of the introducer sheath 1 to the edge 4 of the proximal portion 3, is selected such that a sealing device being introduced into the introducer sheath 1 can be deployed at the desired location inside the vessel 10.

Figure 6:
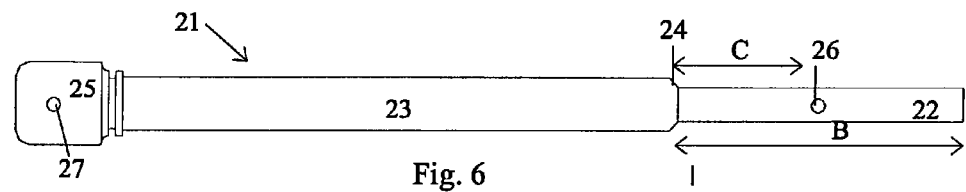
FIG. 6 illustrates a second embodiment of an introducer sheath according to the present invention.

Now with reference to FIG. 6, where a second embodiment of an introducer sheath 21 according to the present invention is illustrated. Like introducer sheath 1, the introducer sheath 21 has a distal portion 22 with a first diameter and proximal portion 23 with a second diameter. As for introducer sheath 1, the diameter of the proximal portion 23 is larger than the diameter of the distal portion 22, or, more specifically, the diameter of the distal portion 22 is adapted to be smaller than the diameter of a puncture hole, whereas the diameter of the proximal portion 23 is adapted to be larger than the diameter of the puncture hole. In FIG. 6 the distal edge of the proximal portion 23 has been marked with 24, and the distance from the distal end of the introducer sheath 21 to the edge 24 of the proximal portion 23 has been denoted with the letter B. The introducer sheath 21 comprises also a hub 25, which is provided in the proximal end of the introducer sheath 21, for connection to some kind of closure and sealing system. Unlike introducer sheath 1, the introducer sheath 21 comprises further two holes, a first hole 26 in the distal portion 22 and a second hole 27 in the hub 25 in the proximal portion 23. The two holes 26, 27 are in fluid communication with each other through a canal 28. The canal 28, which is not shown in FIG. 6, is provided in the wall of the introducer sheath 21. In FIG. 6, the distance from the hole 26 in the distal portion 22 to the edge 24 of the proximal portion 23 has been marked with the letter C. The purposes of these two holes 26, 27 as well as the proper choice of the length C will be described below In FIG. 7, the introducer sheath 21 has been inserted from the skin 29 of a patient, through tissue 30 and through the wall 31 of a blood vessel 32. The introducer sheath 21 is positioned by means of the same positioning operation as was illustrated in FIG. 3 to FIG. 5, and the introducer sheath 21 of FIG. 7 is therefore in the same position as the introducer sheath 1 of FIG. 5. When in the position illustrated in FIG. 7, with the edge 24 of the enlarged proximal portion 23 being in contact with the outer surface of the vessel wall 31, blood can flow into the hole 26 in the distal portion 22, through the canal 28 and out from the hole 27 in the hub 25 provided at the end of the proximal portion 23. Preferably, the distance from the hole 26 in the distal portion 22 to the edge 24 of the proximal portion 23, i.e. the length C, is adapted to be slightly larger than the thickness of the vessel wall 31. By observing a flow of blood from the hole 27, a user is thereby provided with a verification that the edge 24 of the proximal portion 23 is in contact with the outer surface of the vessel wall 31. As before, by choosing a suitable length B for the distal portion 22, a sealing device introduced in the introducer sheath 21 can be deployed at the desired location inside the blood vessel 32.

For the specific embodiment of an introducer sheath described above, the actual sealing of the puncture hole in the wall of the blood vessel is illustrated in FIG. 8 to FIG. 12. This method and the corresponding sealing device are described in the above-mentioned WO 0078226 A1, and will only be very briefly described herein. It should, however, be clear that the first and second embodiments of the introducer sheath according to the present invention can be used together with any device or method which, as a starting point, requires an introducer sheath inserted in a vessel, with the distal end of the introducer sheath being at a known distance from the wall of the vessel.

In FIG. 8 is illustrated how a tool 41 is connected to the introducer sheath 21. The tool 41 comprises basically an elongated feeder means 42, an inner seal 43 and a locking member 44. In the position illustrated in FIG. 9, the feeder means 42 has been pushed into the introducer sheath 21 such that the inner seal 43 has been deployed inside the blood vessel 32, while the locking member 44 is still folded inside the introducer sheath 21, as can be seen through a cut-away section in the distal portion of the introducer sheath 21. In the next step, which is illustrated in FIG. 10, the tool 41 is retracted such that the inner seal 43 is held taut against the inner surface of the vessel wall 31. Thereafter, the feeder means 42 is pushed forward so that the locking member 44 is pushed into position against the outer surface of the vessel wall 31, as is illustrated in FIG. 11. In a final step, which is illustrated in FIG. 12, the tool 41 is retracted, thereby leaving the inner seal 43 connected to the locking member 44 by means of a suture 45 or the like.

Figure 13:
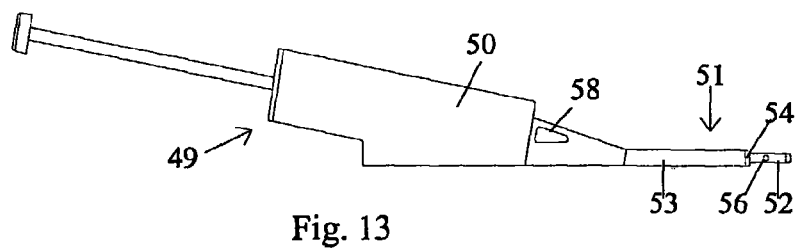
FIG. 13 illustrates an embodiment of an introducer sheath being an integrated part of a tool for closing a puncture hole in a vessel.

The introducer sheaths 1 and 21, shown in FIG. 1 and FIG. 6, respectively, have been described as separate items, to which a tool for closing a puncture wound can be connected, as is illustrated in FIG. 8. The introducer sheaths described above have, however, no features which require that they actually are separate items. On the contrary, an introducer sheath according to the present invention can constitute an integrated part of a tool for closing a puncture wound, and in FIG. 13 such a tool 49 for closing a puncture wound is illustrated. The tool 49 comprises basically a housing 50 and a distal introducer sheath 51. The introducer sheath 51 has a distal portion 52 with a first diameter and a proximal portion 53 with a second diameter, the first diameter being adapted to be smaller than the diameter of a puncture hole and the second diameter being adapted to be larger than the diameter of the puncture hole. In FIG. 13, the distal edge of the proximal portion 53 has been marked with 54. The distal portion 52 is provided with a first hole 56, which through a canal 57 (not shown in FIG. 13) is in fluid communication with a second hole 58 provided in the housing 50.

Figure 14:
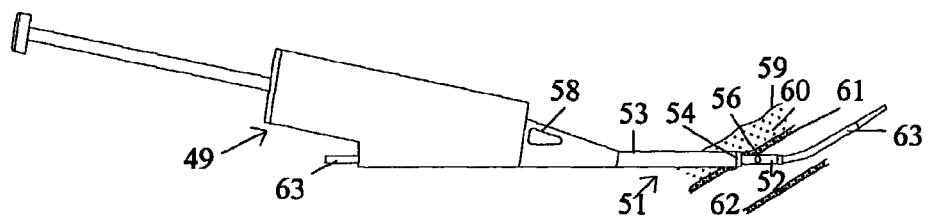
FIG. 14 shows the introducer sheath of FIG. 13 inserted into a blood vessel.

In FIG. 14, the introducer sheath 51 has, over a guide rod 63, been inserted from the skin 59 of a patient, through tissue 60 and through the wall 61 of a blood vessel 62. The introducer sheath 51 is positioned by means of the same positioning operation as was illustrated in FIG. 3 to FIG. 5, and the introducer sheath 51 of FIG. 14 is therefore in the same position as the introducer sheath 1 of FIG. 5, with the difference that the introducer sheath 51 is a part of a tool 49 for closing a puncture wound rather than being a separate introducer. When in the position illustrated in FIG. 14, with the edge 54 of the enlarged proximal portion 53 being in contact with the outer surface of the vessel wall 61, blood can flow into the hole 58 in the distal portion 52, through the canal 57 and into the internal cavity provided in the housing 50. Preferably, the distance from the hole 58 in the distal portion 52 to the edge 54 of the proximal portion 53 is adapted to be slightly larger than the thickness of the vessel wall 61. By observing a flow of blood from the hole 58 in the housing 50, a user is provided with a verification that the edge 54 of the proximal portion 53 is in contact with the outer surface of the vessel wall 61. As before, by choosing a suitable length of the distal portion 52, a sealing device introduced in the introducer sheath 51 can be deployed at the desired location inside the blood vessel 62.

Although the present invention has been described with reference to specific embodiments, also shown in the appended drawings, it will be apparent for those skilled in the art that many variations and modifications can be done within the scope of the invention as described in the specification and defined with reference to the following claims. So could, for example, the canal, which leads blood from a hole in the distal portion of the introducer sheath to the proximal portion, instead of being provided in the wall of the introducer sheath be provided as a longitudinal recess or hole in the dilator or guide rod over which the introducer sheath is threaded, i.e. the canal is provided by the combination of a longitudinal recess or hole in the dilator or guide rod and the inner surface of the introducer sheath.

What is claimed is:

1. A method of positioning an introducer sheath with respect to a blood vessel having a puncture hole and deploying a sealing device, comprising:
   providing an introducer sheath having a distal portion with a first diameter and a proximal portion with a second diameter, the first diameter being smaller than the diameter of said puncture hole and the second diameter being larger than the diameter of said puncture hole, the introducer sheath further comprising a transition portion between the distal portion and the proximal portion, wherein the distal portion, the proximal portion, and the transition portion form a monolithic portion of the introducer sheath;
   inserting the introducer sheath into the puncture hole such that the transition portion contacts an outer surface of the blood vessel to stop the proximal portion from entering the blood vessel and to position a distal end of the introducer sheath in the blood vessel such that the distal end of the introducer sheath is positioned at a predetermined distance from the blood vessel wall; and
   deploying a sealing device from an opening at the distal end of the introducer sheath at the predetermined distance from the blood vessel wall into the blood vessel;
   wherein the transition portion is oriented in a radial direction perpendicularly to a longitudinal axis of the introducer sheath.

2. A method according to claim 1, wherein the method further comprises confirming positioning of the distal end by observing fluid flow from the distal portion to the proximal portion at the proximal portion.

3. A method according to claim 2, wherein the introducer sheath further comprises a first hole provided in the distal portion and a second hole provided in the proximal portion, said first and second holes being in fluid communication with each other through a canal, which is provided in the wall of the introducer sheath.

4. A method according to claim 3, wherein the distance from the first hole to the transition portion is slightly larger than the thickness of the vessel wall, so that, when said transition portion is in contact with the outer surface of the vessel wall, fluid can flow into the first hole, through the canal and out from the second hole.

5. A method according to claim 2, wherein the introducer sheath further comprises a first hole provided in the distal portion and a second hole provided in the proximal portion, said first and second holes being in fluid communication with each other through a canal, which is provided by a longitudinal recess or hole in a dilator or guide rod over which the introducer sheath is threaded.

6. A method according to claim 5, wherein the distance from the first hole to the transition portion is slightly larger than the thickness of the vessel wall, so that, when said transition portion is in contact with the outer surface of the vessel wall, fluid can flow into the first hole, through the canal and out from the second hole.

7. A method according to claim 1, wherein the transition portion comprises a step.

8. A method according to claim 1, wherein the transition portion comprises a sudden increase.

9. A method according to claim 1, wherein the transition portion comprises a steep ramp.

10. The method according to claim 1, wherein the transition portion is positioned outside of the blood vessel wall after the inserting step.

11. A method of positioning an introducer sheath with respect to a blood vessel having a puncture hole and deploying a sealing device, comprising:
   providing an introducer sheath having a distal portion with a first diameter and a proximal portion with a second diameter, the first diameter being smaller than the diameter of said puncture hole and the second diameter being larger than the diameter of said puncture hole, the introducer sheath further comprising a transition portion between the distal portion and the proximal portion, wherein the distal portion, the proximal portion, and the transition portion form a monolithic portion of the introducer sheath;
   inserting the introducer sheath into the puncture hole such that the transition portion contacts an outer surface of the blood vessel to stop the proximal portion from entering the blood vessel and to position a distal end of the introducer sheath in the blood vessel such that the distal end of the introducer sheath is positioned at a predetermined distance from the blood vessel wall; and
   deploying a sealing device from an opening at the extreme distal end of the introducer sheath at the predetermined distance from the blood vessel wall into the blood vessel;
   wherein the transition portion is oriented in a radial direction perpendicularly to a longitudinal axis of the introducer sheath.

12. A method according to claim 11, wherein the method further comprises confirming positioning of the distal end by observing fluid flow from the distal portion to the proximal portion at the proximal portion.

13. A method according to claim 12, wherein the introducer sheath further comprises a first hole provided in the distal portion and a second hole provided in the proximal portion, said first and second holes being in fluid communication with each other through a canal, which is provided in the wall of the introducer sheath.

14. A method according to claim 13, wherein the distance from the first hole to the transition portion is slightly larger than the thickness of the vessel wall, so that, when said transition portion is in contact with the outer surface of the vessel wall, fluid can flow into the first hole, through the canal and out from the second hole.

15. A method according to claim 12, wherein the introducer sheath further comprises a first hole provided in the distal portion and a second hole provided in the proximal portion, said first and second holes being in fluid communication with each other through a canal, which is provided by a longitudinal recess or hole in a dilator or guide rod over which the introducer sheath is threaded.

16. A method according to claim 15, wherein the distance from the first hole to the transition portion is slightly larger than the thickness of the vessel wall, so that, when said transition portion is in contact with the outer surface of the vessel wall, fluid can flow into the first hole, through the canal and out from the second hole.

17. A method according to claim 11, wherein the transition portion comprises a step.

18. A method according to claim 11, wherein the transition portion comprises a sudden increase.

19. A method according to claim 11, wherein the transition portion comprises a steep ramp.

20. The method according to claim 11, wherein the transition portion is positioned outside of the blood vessel wall after the inserting step.

* * * * *